United States Patent
Yoshida

(10) Patent No.: US 9,429,535 B2
(45) Date of Patent: Aug. 30, 2016

(54) HUMIDITY DETERMINING DEVICE AND ENVIRONMENTAL TESTER INCLUDING THE SAME

(71) Applicant: NAGANO SCIENCE CO., LTD., Osaka (JP)

(72) Inventor: Hidetoshi Yoshida, Osaka (JP)

(73) Assignee: Nagano Science., Ltd., Osaka (JP)

( * ) Notice: Subject to any disclaimer, the term of this patent is extended or adjusted under 35 U.S.C. 154(b) by 0 days.

(21) Appl. No.: 14/470,177

(22) Filed: Aug. 27, 2014

(65) Prior Publication Data

US 2014/0369888 A1 Dec. 18, 2014

Related U.S. Application Data

(63) Continuation of application No. PCT/JP2012/007991, filed on Dec. 13, 2012.

(30) Foreign Application Priority Data

Mar. 5, 2012 (JP) ................... 2012-048262

(51) Int. Cl.
*G01N 27/00* (2006.01)
*G01N 27/27* (2006.01)
(Continued)

(52) U.S. Cl.
CPC .......... *G01N 27/121* (2013.01); *G01N 17/002* (2013.01); *G01N 27/126* (2013.01); *G01N 27/225* (2013.01)

(58) Field of Classification Search
CPC . G01N 27/121; G01N 27/126; G01N 17/002
See application file for complete search history.

(56) References Cited

U.S. PATENT DOCUMENTS

| 4,793,181 A * | 12/1988 | Djorup ........................ 73/335.02 |
| 2010/0223944 A1* | 9/2010 | Tsujimoto et al. ............. 62/264 |
| 2011/0213501 A1 | 9/2011 | Jin et al. |

FOREIGN PATENT DOCUMENTS

| CN | 102197266 A | 9/2011 |
| JP | 03-137553 | 6/1991 |

(Continued)

OTHER PUBLICATIONS

International Search Report for corresponding International Application No. PCT/JP2012/007991 mailed Feb. 12, 2013.

(Continued)

*Primary Examiner* — Lyle Alexander
*Assistant Examiner* — Robert Eom
(74) *Attorney, Agent, or Firm* — Renner, Otto, Boisselle & Sklar, LLP

(57) ABSTRACT

A humidity determining device 20 includes first and second humidity determining sensors 17, 18 and a control unit 21. When the first and second humidity determining sensors 17, 18 react with a chemical substance, the humidity determining performance of the first humidity determining sensor 17 and the humidity determining performance of the second humidity determining sensor 18 change with time at different amounts of change. The control unit 21 computes a difference value between a first humidity value and a second humidity value determined by the first and second humidity determining sensors 17, 18. When the difference value is greater than a predetermined reference value, the control unit 21 outputs an anomaly signal indicating that the humidity determining performance of at least one of the first or second humidity determining sensors 17, 18 has been reduced.

3 Claims, 4 Drawing Sheets

(51) Int. Cl.
*G01N 27/12* (2006.01)
*G01N 17/00* (2006.01)
*G01N 27/22* (2006.01)

(56) References Cited

FOREIGN PATENT DOCUMENTS

| | | |
|---|---|---|
| JP | 07-140061 | 6/1995 |
| JP | 2010-237130 | 10/2010 |
| JP | 2011-196875 | 10/2011 |
| WO | WO 2007/134621 A1 | 11/2007 |

OTHER PUBLICATIONS

Form PCT/ISA/237 for corresponding International Application No. PCT/JP2012/007991 dated Feb. 12, 2013.

Extended European Search Report dated Nov. 16, 2015 for corresponding European Application No. 12870508.4.

Kurosawa et al., "A thin-film polysulfone-based capacitive-type relative-humidity sensor", Sensors and Actuators B: Chemical: International Journal Devoted to Research and Development of Physical and Chemical Transducers, Elsevier S. A, CH, vol. 25, No. 1-3, Apr. 1, 1995, pp. 692-695.

* cited by examiner

HUMIDITY DETERMINING DEVICE AND ENVIRONMENTAL TESTER INCLUDING THE SAME

CROSS-REFERENCE TO RELATED APPLICATIONS

This is a continuation of International Application No. PCT/JP2012/007991 filed on Dec. 13, 2012, which claims priority to Japanese Patent Application No. 2012-048262 filed on Mar. 5, 2012. The entire disclosures of these applications are incorporated by reference herein.

BACKGROUND

The present disclosure relates to humidity determining devices and environmental testers including the same.

For example, an environmental tester including a thermostat-humidistat container (chamber) has been used for stability tests of pharmaceuticals, or the like in order to test the performance of a product under predetermined temperature and predetermined humidity. In the environmental tester, a temperature sensor and a humidity sensor are provided in a test chamber of a thermostat-humidistat container surrounded by adiabatic walls, and an air conditioner including a refrigerator, a humidifier, and a heater is controlled based on values measured by these sensors. This allows circulation of air between the container and the air conditioner so that the temperature and the humidity in the container are kept to target temperature and target humidity, respectively (see, for example, Japanese Unexamined Patent Publication No. H07-140061).

In this case, macromolecule capacitive sensors are widely used as the humidity sensors. Such a macromolecule capacitive humidity sensor includes moisture-sensitive macromolecules provided on an electrode, and determines the humidity in the test chamber by measuring the dielectric constant of the moisture-sensitive macromolecules which changes according to the amount of moisture adsorbed onto the moisture-sensitive macromolecules.

SUMMARY

Incidentally, in a conventional environmental tester, a gas containing a predetermined chemical substance may be generated from a sample placed in the test chamber. The chemical substance may react with the moisture-sensitive macromolecules of the macromolecule capacitive humidity sensor, so that the humidity determining performance of the macromolecule capacitive humidity sensor may change with time. When the humidity determining performance of the humidity sensor is reduced, a measurement error becomes large, so that the humidity in the test chamber can no longer be correctly determined.

In view of the foregoing, the present disclosure describes a technique for allowing easy determination of a reduction in humidity determining performance of a humidity determining section for determining the humidity in a test chamber.

The present disclosure is directed to a humidity determining device configured to determine the humidity in a chamber in which a predetermined chemical substance is contained, the humidity determining device having the following features.

That is, a first aspect of the present disclosure provides a configuration which includes: a first humidity determining section configured to determine the humidity in a test chamber and have humidity determining performance which changes with time due to a reaction of the first humidity determining section with a chemical substance; a second humidity determining section disposed near the first humidity determining section and configured to determine the humidity in the test chamber and have humidity determining performance which changes with time due to a reaction of the second humidity determining section with the chemical substance at an amount of change which is different from an amount of change in the humidity determining performance of the first humidity determining section; and a controller configured to receive a first humidity value determined by the first humidity determining section and a second humidity value determined by the second humidity determining section, wherein the controller is configured to compute a difference value between the first humidity value and the second humidity value and output, when the difference value is greater than a predetermined reference value, an anomaly signal indicating that the humidity determining performance of at least one of the first humidity determining section or the second humidity determining section has been reduced.

According to the first aspect of the present disclosure, the humidity determining performance of the first humidity determining section and the humidity determining performance of the second humidity determining section change with time at different amounts of change when the first humidity determining section and the second humidity determining section react with a chemical substance. When the first humidity value and the second humidity value respectively determined by the first humidity determining section and the second humidity determining section are input to the controller, the controller computes a difference value between the first humidity value and the second humidity value. When the difference value is greater than a predetermined reference value, an anomaly signal indicating that the humidity determining performance of at least one of the first humidity determining section or the second humidity determining section has been reduced is output.

With this configuration, it is possible to easily determine that the humidity determining performance of at least one of the first humidity determining section or the second humidity determining section has been reduced. Specifically, when the humidity in the test chamber is determined by only one humidity determining section, it is not possible to recognize that the humidity determining performance of the humidity determining section has been changed with time due to a reaction of the humidity determining section with a chemical substance. Thus, a measurement error becomes large, so that it is difficult to correctly determine the humidity in the test chamber.

In contrast, in the present disclosure, the first and second humidity determining sections having different amounts of change in humidity determining performance which change with time due to reactions of the first and second humidity determining sections with a chemical substance determine the humidity in the test chamber. Therefore, comparing a difference value between first and second humidity values determined by the first and second humidity determining sections with a predetermined reference value allows easy determination of a reduction in humidity determining performance of at least one of the first or second humidity determining sections, so that the humidity determining section can be readily replaced.

Since the humidity determining device according to the first aspect of the present disclosure can be added to an existing environmental tester by retrofitting, it is not necessary to replace the environmental tester, so that the humidity determining performance in the test chamber containing a predetermined chemical substance can be improved with low costs.

A second aspect of the present disclosure provides a configuration in which, in the first aspect of the disclosure, the first humidity determining section is configured to determine the first humidity value to be greater than an actual value of the humidity in the test chamber due to the reaction of the first humidity determining section with the chemical substance, and the second humidity determining section is configured to determine the second humidity value to be less than the actual value of the humidity in the test chamber due to the reaction of the second humidity determining section with the chemical substance.

In the second aspect of the present disclosure, when the first and second humidity determining sections react with a chemical substance, the first humidity determining section determines the first humidity value to be greater than the actual humidity in the test chamber, and the second humidity determining section determines the second humidity value to be less than the actual humidity.

With this configuration, when the difference value between the first humidity value and the second humidity value is computed, a relatively high value is obtained as the difference value. Thus, a reduction in humidity determining performance of the first and second humidity determining sections can be more accurately determined.

A third aspect of the present disclosure is an environmental tester including: the humidity determining device of the first aspect of the disclosure; a thermostat-humidistat container including a test chamber; an air conditioner configured to adjust a temperature and a humidity in the test chamber; and a warning device configured to perform predetermined warning operation in response to the anomaly signal output from the humidity determining device.

In the third aspect of the present disclosure, when an anomaly signal is output from the humidity determining device, the warning device performs predetermined warning operation. With this configuration, it is possible to easily determine, with reference to the warning operation, that the humidity determining performance of at least one of the first or second humidity determining sections has been reduced. The warning device is composed of, for example, an alarm or a signal, and can warn an operator a reduction in humidity determining performance by sounding the alarm or turning on the signal. Another example of the warning operation is displaying a message indicating a reduction in humidity determining performance on a display or sending the message to a manager in a remote place via a network.

In the present disclosure, the first and second humidity determining sections having different amounts of change in humidity determining performance which change with time due to reactions of the first and second humidity determining sections with a chemical substance determine the humidity in the test chamber. Therefore, comparing a difference value between first and second humidity values respectively determined by the first and second humidity determining sections with a predetermined reference value allows easy determination of a reduction in humidity determining performance of at least one of the first or second humidity determining sections, so that the humidity determining section can be readily replaced.

Since the humidity determining device according to the first aspect of the present disclosure can be added to an existing environmental tester by retrofitting, it is not necessary to replace the environmental tester, so that the humidity determining performance in the test chamber containing a predetermined chemical substance can be improved with low costs.

DETAILED DESCRIPTION

Embodiments according to the present disclosure will be described with reference to the drawings. The above-described embodiments have been set forth merely for the purposes of preferred examples in nature, and are not intended to limit the scope, applications, and use of the disclosure.

Figure 1:
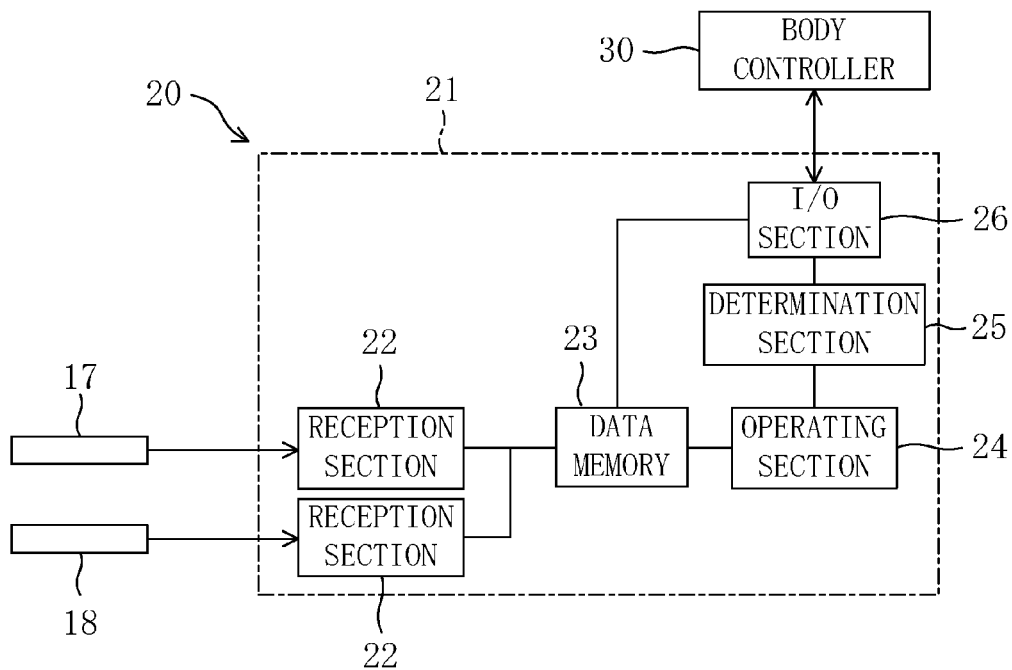
FIG. 1 is a functional block diagram illustrating an internal configuration of a humidity determining device according to an embodiment of the present disclosure.

FIG. 1 is a functional block diagram illustrating an internal configuration of a humidity determining device according to an embodiment of the present disclosure. As illustrated in FIG. 1, a humidity determining device 20 includes a first humidity determining sensor 17, a second humidity determining sensor 18, and a control unit 21.

The first humidity determining sensor 17 includes a macromolecule capacitive sensor. Specifically, the first humidity determining sensor 17 includes moisture-sensitive macromolecules provided on an electrode, and determines humidity by measuring a dielectric constant of the moisture-sensitive macromolecules. The dielectric constant changes according to the amount of moisture adsorbed onto the moisture-sensitive macromolecules. A first humidity value which is a value of the humidity determined by the first humidity determining sensor 17 is sent to the control unit 21.

The second humidity determining sensor 18 includes a macromolecule capacitive sensor and is disposed near the first humidity determining sensor 17. A second humidity value which is a value of humidity determined by the second humidity determining sensor 18 is sent to the control unit 21. Here, the amount of change at which the humidity determining performance of the second humidity determining sensor 18 changes with time due to a reaction of the second humidity determining sensor 18 with a predetermined chemical substance is different from the amount of change at which the humidity determining performance of the first humidity determining sensor 17 changes with time due to a reaction of the first humidity determining sensor 17 with the predetermined chemical substance.

Figure 2:
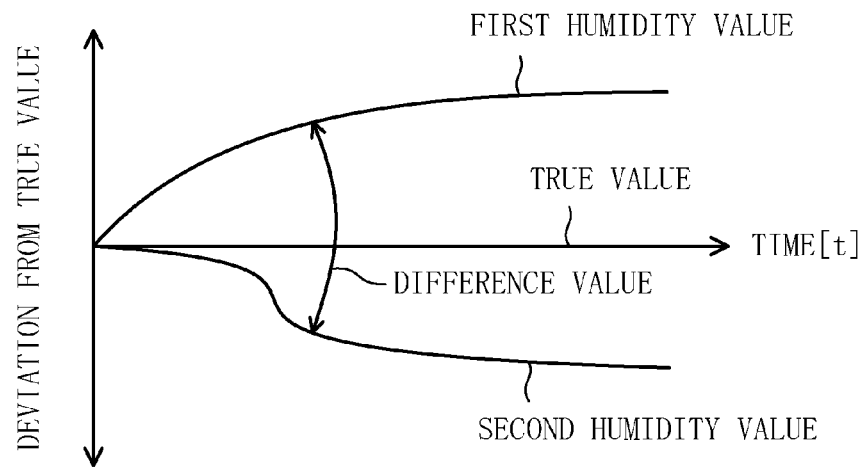
FIG. 2 is a graph illustrating the difference in amount of change in humidity determining performance when the first and second humidity determining sensors react with a chemical substance.

Specifically, as illustrated in FIG. 2, the first humidity determining sensor 17 is a sensor which tends to exhibit deviation toward higher values than an actual humidity (true value) in the test chamber S when the first humidity determining sensor 17 reacts with a chemical substance. That is, the first humidity determining sensor 17 determines the first humidity value to be greater than the actual humidity.

On the other hand, the second humidity determining sensor 18 is a sensor which tends to exhibit deviation toward lower values than the true value when the second humidity determining sensor 18 reacts with the chemical substance. That is, the second humidity determining sensor 18 determines the second humidity value to be less than the actual humidity.

The tendency of deviation from the true value in the case of reactions of the first and second humidity determining sensors 17, 18 with the chemical substance is a mere example, and the present disclosure is not limited to this embodiment. For example, also when both the first and second humidity determining sensors 17, 18 are sensors which tend to exhibit deviation toward greater values than the true value, a difference value can be computed as long as the amounts of deviation of the sensors are different from each other.

As illustrated in FIG. 1, the control unit 21 includes reception sections 22 configured to receive signals from the first and second humidity determining sensors 17, 18, a data memory 23 configured to store the signals received by the reception sections 22, an operating section 24 configured to compute the difference value between the first humidity value and the second humidity value stored in the data memory 23, a determination section 25 configured to compare the difference value computed by the operating section 24 with a predetermined reference value, and an I/O section 26 configured to send the first and second humidity values determined by the first and second humidity determining sensors 17, 18 and a result of the determination by the determination section 25 to a body controller 30 of an environmental tester 10 which will be described later.

When the difference value between the first and second humidity values is greater than the predetermined reference value, the determination section 25 outputs an anomaly signal indicating that the humidity determining performance of at least one of the first or second humidity determining sensors 17, 18 has been reduced. The anomaly signal output from the determination section 25 is sent to the body controller 30 of the environmental tester 10 via the I/O section 26.

Figure 3:
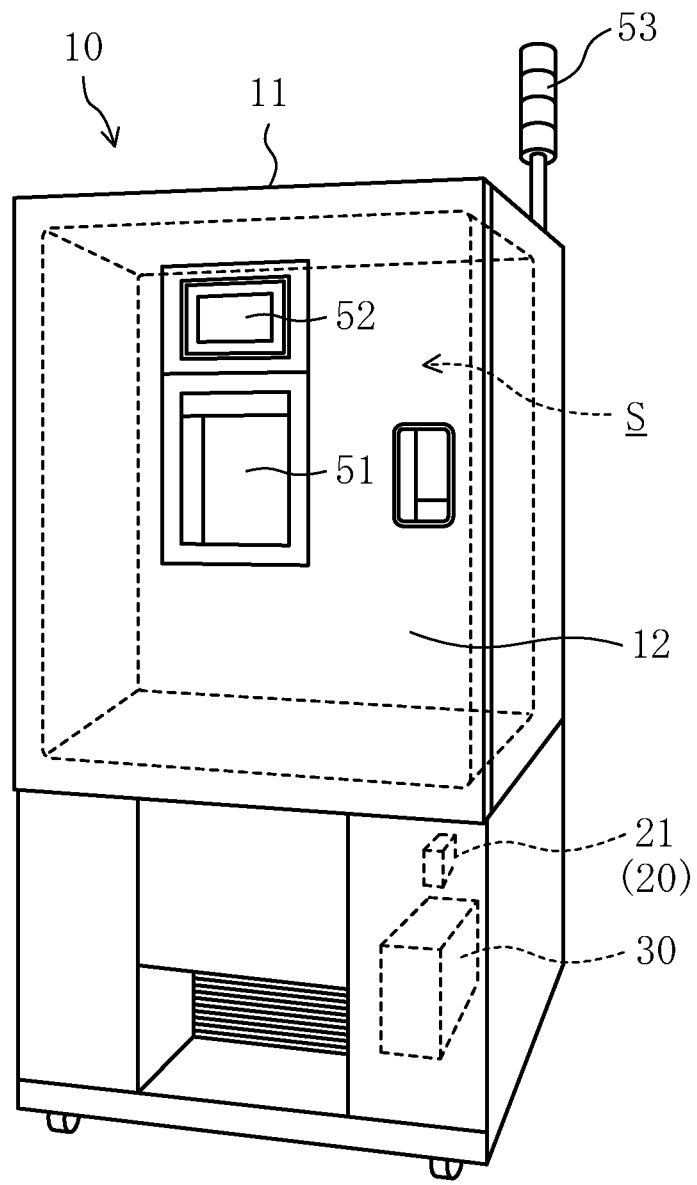
FIG. 3 is a perspective view illustrating a configuration of a thermostat-humidistat bath in an environmental tester.

FIG. 3 is a perspective view illustrating a configuration of a thermostat-humidistat container in an environmental tester. As illustrated in FIG. 3, a thermostat-humidistat container 11 (chamber) is used for stability tests of pharmaceuticals, for example. For this reason, temperature and humidity in a test chamber S are stably kept within the predetermined ranges, respectively.

The thermostat-humidistat container 11 has a contour in the shape of a substantially rectangular parallelepiped, and a door 12 extending from an upper end to a center section of a front face of the thermostat-humidistat container 11 is attached to the thermostat-humidistat container 11 to be able to open and close. A consol panel 51 for, for example, setting target values for controlling temperature and humidity and a display 52 for displaying the set values, and the like are disposed to be aligned in the vertical direction on a front face of the door 12.

Figure 4:
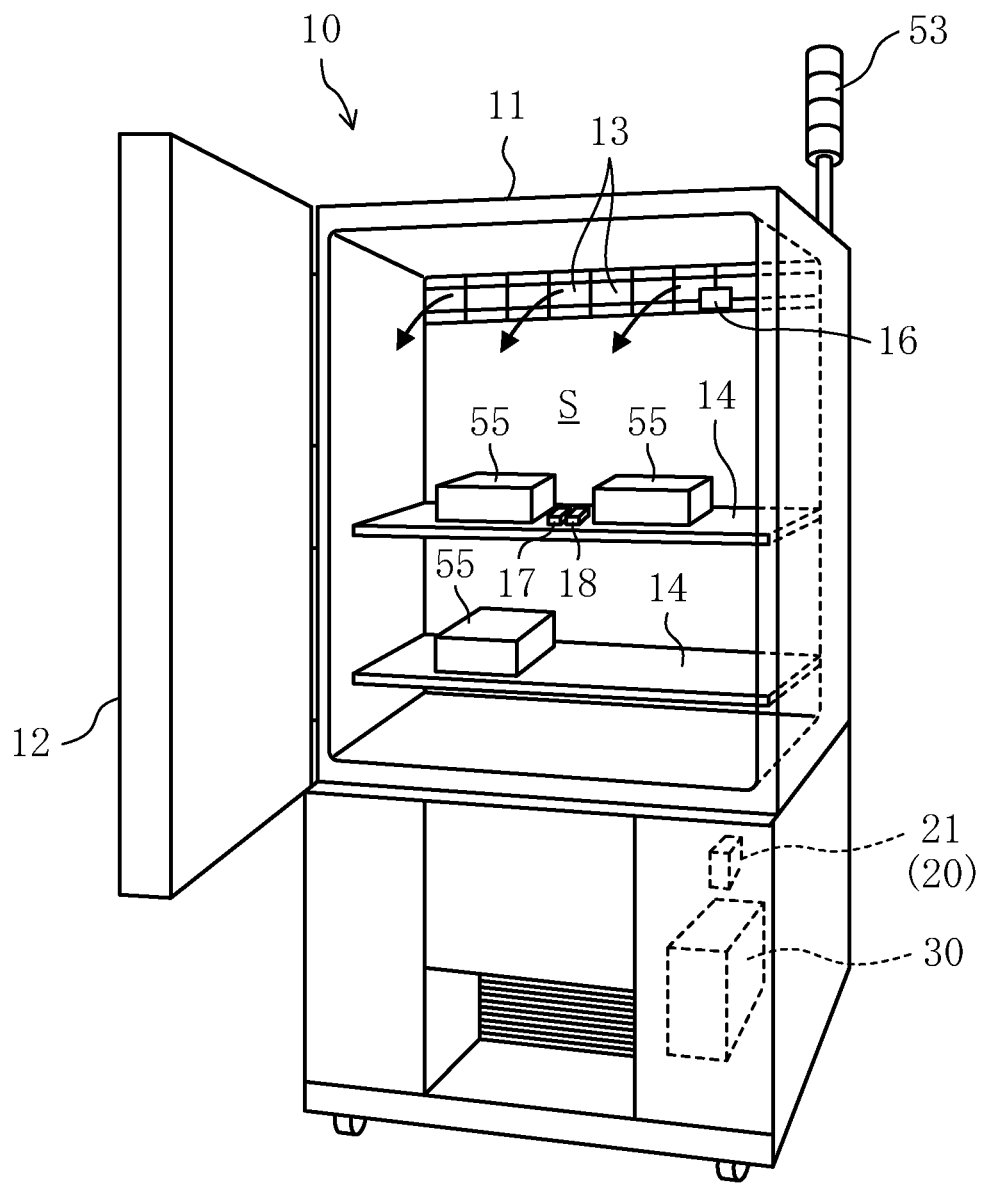
FIG. 4 is a perspective view illustrating a configuration of a test chamber of the thermostat-humidistat bath in the environmental tester.

As illustrated in FIG. 4, the door 12 of the thermostat-humidistat container 11 is opened to access to the test chamber S which is in the shape of a substantially rectangular parallelepiped and is formed in the thermostat-humidistat container 11, so that a sample 55 can be placed in the test chamber S, or a sample 55 placed in the test chamber can be taken out. An air outlet 13 is formed in an upper portion of a wall surface at the depth of the test chamber S, and through the air outlet 13, conditioned air of adjusted temperature and humidity is discharged to the test chamber S from an air conditioner 15 (see FIG. 5) including a refrigerator, a humidifier, a heater, etc. An air inlet (not shown) is formed in a lower portion of the wall surface at the depth of the test chamber S, and air in the test chamber S is sucked through the air inlet and is then supplied to the air conditioner 15.

In the thermostat-humidistat container 11, air is circulated between the test chamber S and the air conditioner 15, thereby stably keeping the temperature and the humidity in the test chamber S within the predetermined ranges, respectively. Note that the thermostat-humidistat container 11 defines a closed space between the test chamber S and the air conditioner 15.

In the test chamber S, two shelf boards 14 in the embodiment illustrated in FIG. 4 are arranged to be aligned in the vertical direction, and samples 55 are placed on the shelf boards 14. The number and the position of the shelf board 14 are not limited to this embodiment, but may be suitably determined.

At a position corresponding to the center of the test chamber S (a center position of the shelf board 14 in the embodiment illustrated in FIG. 4), the first and second humidity determining sensors 17, 18 are disposed. The first and second humidity determining sensors 17, 18 are sensors configured to measure the humidity in the test chamber S. The first and second humidity values determined by the first and second humidity determining sensors 17, 18 are sent to the control unit 21.

The thermostat-humidistat container 11 includes a temperature and humidity sensor 16 arranged at the air outlet 13, and based on values measured by the temperature and humidity sensor 16, the temperature, the relative humidity, and the absolute humidity of air discharged through the air outlet 13 are determined. The arrangement position of the temperature and humidity sensor 16 is not limited to the position near the air outlet 13, but the temperature and humidity sensor 16 may be arranged near the air inlet.

Measured signals from the temperature and humidity sensor 16 are sent to the body controller 30 disposed at a lower portion of the thermostat-humidistat container 11. The body controller 30 controls the air conditioner 15 based on the values measured by the temperature and humidity sensor 16 in such a manner that the temperature and the humidity in the test chamber S match the predetermined temperature and the predetermined humidity, respectively. Although the first and second humidity determining sensors 17, 18 are used for monitoring the humidity in the test chamber S in the present embodiment, the first and second humidity determining sensors 17, 18 may be used to control the air conditioner 15 together with the temperature and humidity sensor 16.

Figure 5:
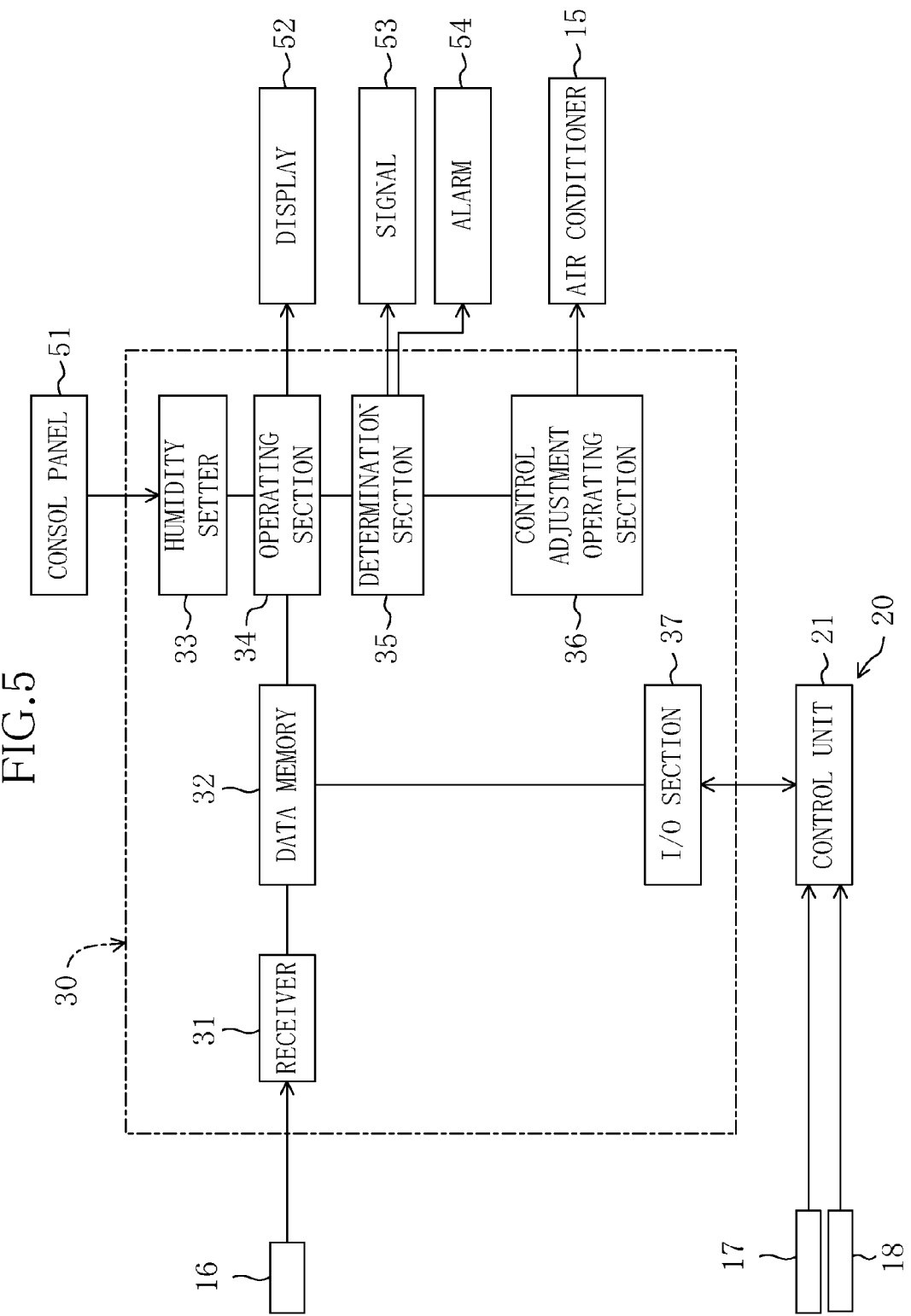
FIG. 5 is a functional block diagram illustrating an internal configuration of the thermostat-humidistat bath in the environmental tester.

FIG. 5 is a functional block diagram illustrating an internal configuration of the thermostat-humidistat container in the environmental tester. As illustrated in FIG. 5, the body controller 30 includes a receiver 31 for receiving the signals from the temperature and humidity sensor 16, and a data memory 32 for storing the signals received by the receiver 31.

The body controller 30 further includes a temperature and humidity setter 33 and an operating section 34. The temperature and humidity setter 33 sets target values for controlling the temperature and the humidity in the test chamber S based on operation signals from the consol panel 51, through which an operator sets the target temperature and humidity. The operating section 34 receives signals from the temperature and humidity setter 33 and the data memory 32, and carries out various operations for controlling the air conditioner 15 as described below. Where necessary, the results of the operations are shown on the display 52 provided on the door 12 of the thermostat-humidistat chamber 11.

The operating section 34 computes the differences of the values of the temperature and the humidity measured by the first temperature and humidity sensor 16 from the set values, thereby generating a correction value. A determination section 35 determines the differences of the values measured by the first temperature and humidity sensor 16 from the set values.

The body controller 30 includes a control adjustment operating section 36 which carries out an operation for control adjustments of the air conditioner 15.

The body controller 30 further includes an I/O section 37 for communication with a humidity determining device 20. A control program (software) has been updated so that the body controller 30 can perform warning operation based on an anomaly signal output from the humidity determining device 20.

The anomaly signal output from the humidity determining device 20 is input to the body controller 30 via the I/O section 26. Based on the anomaly signal, the body controller 30 operates a signal 53 and an alarm 54 to warn an operator. The warning operation may be displaying, on the display 52, a message indicating that the humidity determining performance of at least one of the first or second humidity determining sensors 17, 18 has been reduced, or may be sending the message to a manager in a remote place via a network.

—Operating Method—

Next, a method for operating the environmental tester 10 will be described. The door 12 of the thermostat-humidistat container 11 is opened to place a sample 55 of the environmental test on the shelf board 14 disposed in the test chamber S.

Target values are input via the consol panel 51 disposed on the front face of the door 12. Here, an operator can see the target values displayed on the display 52 to check whether or not the operation is correct.

During operation of the environmental tester 10, conditioned air of adjusted temperature and adjusted humidity is discharged to the test chamber S from the air conditioner 15 through the air outlet 13. Air is supplied to the air conditioner 15 through the air inlet disposed in the lower portion of the wall surface at the depth in the test chamber S. The environmental tester 10 is operated such that while the air is circulated in this way between the test chamber S and the air conditioner 15, the conditioned air whose temperature and humidity have been adjusted in the air conditioner 20 is supplied to the test chamber S in such a manner that the temperature and the humidity in the test chamber S match the input target values.

Temperature data and humidity data measured by the temperature and humidity sensor 16 disposed near the air outlet 13 in the test chamber S are stored in the data memory 32 via the receiver 31 of the body controller 30. Timing at which the data signals are stored in the data memory 32 occurs in a predetermined cycle.

On the other hand, humidity data measured by the first humidity determining sensor 17 disposed in the test chamber S and humidity data measured by the second humidity determining sensor 18 disposed in the test chamber S are stored in the data memory 23 via the respective reception sections 22 of the control unit 21.

The operating section 24 computes a difference value between the first and second humidity values of the first and second humidity determining sensors 17, 18 stored in the data memory 23. The determination section 25 compares the difference value with the predetermined reference value for determination. When the difference value is greater than the reference value, it is determined that the humidity determining performance has been reduced due to an increase in deviation from the true value because of a reaction of at least one of the first or second humidity determining sensors 17, 18 with a chemical substance, and an anomaly signal indicating the reduction in humidity determining performance is output. The anomaly signal output from the determination section 25 is sent to the body controller 30 of the environmental tester 10 via the I/O section 26.

Based on the anomaly signal, the body controller 30 operates the signal 53 and the alarm 54 to warn an operator. A message indicating a reduction in humidity determining performance may be displayed on the display 52, or may be sent to a manager in a remote place via a network.

As described above, in the humidity determining device 20 according to the present embodiment, the humidity in the test chamber S is determined by the first and second humidity determining sensors 17, 18 having different amounts of change in humidity determining performance, which changes with time, in the case of reactions of the first and second humidity determining sensors 17, 18 with a chemical substance. Thus, a reduction in humidity determining performance of at least one of the first or second humidity determining sensors 17, 18 can be easily determined by comparing the difference value between the first and second humidity values with a predetermined reference value, so that the first and second humidity determining sensors 17, 18 can be readily replaced.

Since the humidity determining device 20 according to the present embodiment can be added to the existing environmental tester 10 by retrofitting, it is not necessary to replace the environmental tester 10, and thus the humidity determining performance in the test chamber S in which a predetermined chemical substance is contained can be easily improved with low costs.

Other Embodiments

The embodiment may have the following configuration.

In the above embodiment, a configuration in which two, the first and second humidity determining sensors 17, 18 respectively determine first and second humidity values to compute a difference value between the first and second humidity values has been described. However, the number of the humidity determining sensors is not limited to that of the embodiment, but three or more humidity determining sensors may be used.

In the above embodiment, the first and second humidity determining sensors 17, 18 are disposed at a position corresponding to the center of the test chamber S (a center position of the shelf board 14 in the embodiment illustrated in FIG. 4). However, this embodiment is a mere example, and the arrangement positions of the first and second humidity determining sensors 17, 18 can be suitably determined.

In the above embodiment, the first and second humidity determining sensors 17, 18 are separate sensors, but a configuration in which one humidity determining sensor includes two humidity determining sections may be possible.

In the above embodiment, a configuration in which the thermostat-humidistat container 11 includes the test chamber S provided therein has been described. However, the size of the test chamber S is not particularly limited. That is, a configuration in which a thermostat-humidistat room includes a test chamber S as a room having a size allowing the entrance of workers is also within the scope of the disclosure.

INDUSTRIAL APPLICABILITY

As described above, the present disclosure provides the highly practical advantage that a reduction in humidity determining performance of a humidity determining sensor for determining the humidity in the test chamber can be easily determined. Thus, the present disclosure is very useful and has a wide industrial applicability.

What is claimed is:

1. A humidity determining device configured to determine a humidity in a test chamber, the humidity in the test chamber having a true value, the humidity determining device comprising:
   a first humidity determining section configured to determine the humidity in the test chamber, the first humidity determining section having a humidity determining performance which changes in amount of deviation relative to the true value with time due to a reaction of the first humidity determining section with a chemical substance contained in the test chamber;
   a second humidity determining section disposed near the first humidity determining section and configured to determine the humidity in the test chamber, the second humidity determining section having a humidity determining performance which changes in amount of deviation relative to the true value with time due to a reaction of the second humidity determining section with the chemical substance, wherein the humidity determining performance of the first humidity determining section changes in amount of deviation relative to the true value with time differently from the changes in amount of deviation relative to the true value with time of the humidity determining performance of the second humidity determining section; and
   a controller configured to receive a first humidity value determined by the first humidity determining section and a second humidity value determined by the second humidity determining section, wherein
   the controller is configured to compute a difference value between the first humidity value and the second humidity value and to output, when a net difference in the amount of deviation of the first humidity determining section and the amount of deviation of the second humidity determining section relative to the true value is greater than a predetermined reference value, an anomaly signal indicating that the humidity determining performance of at least one of the first humidity determining section or the second humidity determining section has been reduced.

2. The humidity determining device of claim 1, wherein the first humidity determining section is configured to determine the first humidity value to be greater than an actual value of the humidity in the test chamber due to the reaction of the first humidity determining section with the chemical substance, and
   the second humidity determining section is configured to determine the second humidity value to be less than the actual value of the humidity in the test chamber due to the reaction of the second humidity determining section with the chemical substance.

3. An environmental tester comprising:
   the humidity determining device of claim 1;
   a thermostat-humidistat container including the test chamber;
   an air conditioner configured to adjust a temperature and a humidity in the test chamber; and
   a warning device configured to perform predetermined warning operation in response to the anomaly signal output from the humidity determining device.

\* \* \* \* \*